(12) United States Patent
Yoshizawa et al.

(10) Patent No.: US 11,484,225 B2
(45) Date of Patent: Nov. 1, 2022

(54) REHABILITATION EVALUATION APPARATUS, REHABILITATION EVALUATION METHOD, AND REHABILITATION EVALUATION PROGRAM

(71) Applicant: TOYOTA JIDOSHA KABUSHIKI KAISHA, Toyota (JP)

(72) Inventors: Shintaro Yoshizawa, Nagoya (JP); Hitoshi Yamada, Nagakute (JP); Alvaro Costa Garcia, Owariasahi (JP); Hiroshi Yamasaki, Nagoya (JP); Matti Sakari Itkonen, Nagoya (JP); Shingo Shimoda, Kasugai (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 460 days.

(21) Appl. No.: 16/027,915

(22) Filed: Jul. 5, 2018

(65) Prior Publication Data

US 2019/0008419 A1  Jan. 10, 2019

(30) Foreign Application Priority Data

Jul. 10, 2017 (JP) .............................. JP2017-134991

(51) Int. Cl.
*A61B 5/11* (2006.01)
*A61B 5/316* (2021.01)
(Continued)

(52) U.S. Cl.
CPC .......... *A61B 5/1124* (2013.01); *A61B 5/1126* (2013.01); *A61B 5/316* (2021.01);
(Continued)

(58) Field of Classification Search
CPC . A61B 5/1124; A61B 5/0488; A61B 5/04012; A61B 5/4848; A61B 5/1126;
(Continued)

(56) References Cited

U.S. PATENT DOCUMENTS

| 2010/0036288 A1* | 2/2010 | Lanfermann | .......... A61B 5/225 600/595 |
| 2011/0004126 A1* | 1/2011 | Einav | ..................... G16H 20/30 600/595 |

(Continued)

FOREIGN PATENT DOCUMENTS

| CN | 103886215 A | 6/2014 |
| JP | 2014-133123 | 7/2014 |

(Continued)

OTHER PUBLICATIONS

Salman et al., "Changes in muscle activation patterns following robot-assisted training of hand function after stroke," 2010 IEEE/RSJ International Conference on Intelligent Robots and Systems, Taipei, 2010, pp. 5145-5150, doi: 10.1109/IROS.2010.5650175 (Year: 2010).*

(Continued)

*Primary Examiner* — Devin B Henson
*Assistant Examiner* — Justin Xu
(74) *Attorney, Agent, or Firm* — Oblon, McClelland, Maier & Neustadt, L.L.P.

(57) ABSTRACT

A rehabilitation evaluation apparatus includes a sensor signal acquisition unit configured to acquire a sensor signal output from a detection sensor, a selection unit configured to select at least one myoelectric signal having a correlation with the sensor signal acquired by the sensor signal acquisition unit from among the plurality of second myoelectric signals on the second-side part acquired by the myoelectric-signal acquisition unit, and a similarity output unit configured to select a first myoelectric signal that has been output from a myoelectric sensor attached in a place that is left-right symmetric to a place of the myoelectric sensor that has output the second correlated myoelectric signal selected by the selection unit from among a plurality of first myoelectric signals on the first-side part acquired by the myoelectric- (Continued)

signal acquisition unit, calculate a similarity between these correlated myoelectric signals, and outputs the calculated similarity.

11 Claims, 6 Drawing Sheets

(51) Int. Cl.
- *A61B 5/389* (2021.01)
- *A61B 5/00* (2006.01)
- *G16H 20/30* (2018.01)
- *G16H 40/63* (2018.01)
- *A61B 5/22* (2006.01)

(52) U.S. Cl.
CPC .......... *A61B 5/389* (2021.01); *A61B 5/4848* (2013.01); *A61B 5/4884* (2013.01); *A61B 5/7246* (2013.01); *G16H 20/30* (2018.01); *G16H 40/63* (2018.01); *A61B 5/221* (2013.01); *A61B 5/6824* (2013.01); *A61B 5/6828* (2013.01); *A61B 5/7275* (2013.01); *A61B 5/742* (2013.01); *A61B 2505/09* (2013.01)

(58) Field of Classification Search
CPC ... A61B 5/7246; A61B 5/4884; A61B 5/6828; A61B 5/6824; A61B 5/221; A61B 5/742; A61B 5/7275; A61B 2505/09; A61B 5/7235; G16H 40/63; G16H 20/30
See application file for complete search history.

(56) References Cited

U.S. PATENT DOCUMENTS

| | | | | |
|---|---|---|---|---|
| 2011/0295127 | A1* | 12/2011 | Sandler | A61B 7/026 600/484 |
| 2012/0172682 | A1* | 7/2012 | Linderman | G06F 3/015 600/300 |
| 2014/0156197 | A1* | 6/2014 | Kim | A61B 5/316 702/19 |
| 2014/0163412 | A1* | 6/2014 | Jacobson | A61B 5/7203 600/546 |
| 2014/0371599 | A1* | 12/2014 | Wu | G06T 7/262 600/476 |
| 2015/0106023 | A1 | 4/2015 | Shimoda et al. | |
| 2017/0143226 | A1* | 5/2017 | Ding | A61B 5/389 |
| 2017/0325705 | A1* | 11/2017 | Ramos Murguialday | A61B 5/316 |
| 2019/0269343 | A1* | 9/2019 | Ramos Murguialday | A61H 1/0237 |

FOREIGN PATENT DOCUMENTS

| | | |
|---|---|---|
| JP | 2015-073805 | 4/2015 |
| JP | 2016-054994 | 4/2016 |
| JP | 2018-038521 | 3/2018 |

OTHER PUBLICATIONS

Costa, A., et al., "Importance of Muscle Selection for EMG Signal Analysis during Upper Limb Rehabilitation of Stroke Patients*", 39th Anual International Conference of the IEEE Engineering Medicine and Biology Society, Jul. 11, 2017, XP033152566, pp. 2510-2513.

* cited by examiner

REHABILITATION EVALUATION APPARATUS, REHABILITATION EVALUATION METHOD, AND REHABILITATION EVALUATION PROGRAM

CROSS REFERENCE TO RELATED APPLICATIONS

This application is based upon and claims the benefit of priority from Japanese patent application No. 2017-134991, filed on Jul. 10, 2017, the disclosure of which is incorporated herein in its entirety by reference.

BACKGROUND

The present disclosure relates to a rehabilitation evaluation apparatus, a rehabilitation evaluation method, and a rehabilitation evaluation program.

There are patients who suffer from hemiplegia in which a part of one of left and right limbs is paralyzed. Apparatuses that assist such patients in doing rehabilitation training are becoming widespread. A training apparatus for evaluating a level of recovery on a non-paralyzed side by making a patient try to do certain rehabilitation training on the non-paralyzed side as well as on a paralyzed side, and then performing a calculation as to how much myoelectric signals obtained on the paralyzed side resemble those obtained on the non-paralyzed side has been known (e.g., Japanese Unexamined Patent Application Publication No. 2015-73805).

SUMMARY

The present inventors have found the following problem. It has become evident that when a patient tries to do rehabilitation training, muscles that work for the trial of the rehabilitation training and ratios at which these muscles work in a coordinated manner differ from one individual to another and also differ according to the environment and the condition under which the patient does the trial. Therefore, it is very difficult to determine in advance which muscles should be chosen to observe their myoelectric potentials according to the trial. When the number of places at which myoelectric potentials are measured is small, there is a high possibility that a muscle(s) that considerably works for the motions in the trial could be overlooked. On the other hand, when the number of places at which myoelectric potentials are measured is increased too much, data on muscles that do not work much for the motions in the trial could become dominant. In either case, it has been difficult to accurately evaluate the level of recovery (hereinafter also referred to as the "recovery level") of a diseased part by comparing myoelectric signals obtained from the paralyzed side with those obtained from the non-paralyzed side.

The present disclosure has been made to solve the above-described problem and an object thereof is to provide a rehabilitation evaluation apparatus and the like capable of accurately evaluating a recovery level of a diseased part in a short time without requiring a troublesome trial-and-error process for adjusting positions of myoelectric-potential sensors every time a patient does rehabilitation training.

A first exemplary aspect is a rehabilitation evaluation apparatus configured to evaluate a level of recovery of a trainee by rehabilitation training, including: a myoelectric-signal acquisition unit configured to acquire a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs; a sensor signal acquisition unit configured to acquire a sensor signal output from a detection sensor, the detection sensor being configured to detect an amount of a change in the second-side part resulting from a comparative motion corresponding to a training motion performed in the first-side part in the rehabilitation training, in which the trainee is a detection target and performs the comparative motion in the second-side part; a selection unit configured to select, as a second correlated myoelectric signal, at least one second myoelectric signal having a correlation with the sensor signal acquired by the sensor signal acquisition unit from among the plurality of second myoelectric signals acquired by the myoelectric-signal acquisition unit; and a similarity output unit configured to select, as a first correlated myoelectric signal, a first myoelectric signal that has been output from a first myoelectric sensor attached in a place that is left-right symmetric to a place of the second myoelectric sensor that has output the second correlated myoelectric signal selected by the selection unit with respect to the limbs from among the plurality of first myoelectric signals acquired by the myoelectric-signal acquisition unit, calculate a similarity between the first and second correlated myoelectric signals, and output the calculated similarity.

According to the rehabilitation evaluation apparatus configured as described above, since myoelectric signals from muscles that considerably works for training motions in rehabilitation training are selected and compared, a recovery level of a diseased part can be accurately evaluated. That is, even when myoelectric sensors are attached in a number of places, myoelectric signals that are not significantly related to the training motions are excluded, thus making it possible to obtain an accurate evaluation result. Further, there is no or small possibility that any myoelectric signal from a muscle that considerably works for the training motions cannot be obtained. Furthermore, since a large number of myoelectric sensors can be attached, there is no need to finely adjust the position of each myoelectric sensor while observing its output through a trial-and-error process. As a result, it is possible to reduce the overall time required for the rehabilitation training.

In the above-described rehabilitation evaluation apparatus, when the trainee tries to perform the training motion repeatedly, the similarity output unit may continuously use an output of the first myoelectric sensor that has output the first correlated myoelectric signal selected once as the first correlated myoelectric signal. By determining the first correlated myoelectric signal in this manner, there is no need to make the trainee perform the comparative motion on the non-paralyzed side every time the trainee does rehabilitation training, thus making it possible to efficiently carry out the rehabilitation training.

Further, the selection unit can calculate a motion frequency of the comparative motion from the sensor signal acquired by the sensor signal acquisition unit and select a myoelectric signal having a predetermined strength or stronger at the motion frequency from among the plurality of second myoelectric signals acquired by the myoelectric-signal acquisition unit as the second correlated myoelectric signal having the correlation with the sensor signal. By evaluating the myoelectric signal in the frequency domain as described above, it is possible to eliminate uncertain factors such as variations in the offset value and the amplitude of the myoelectric signal. Further, a root-mean-square value calculated from sampled values obtained after a filtering process is performed for a target second myoelectric signal may be added to the strength at the motion frequency and a resultant value may be compared with a predetermined value. By taking the amplitude value with respect to the elapsed time for the myoelectric signal, it is possible to select a myoelectric signal from a muscle that considerably affects the training motion.

Further, the similarity output unit preferably calculates, when m selected first correlated myoelectric signals are represented by row vectors $M_1^{(1)}, M_1^{(2)}, \ldots,$ and $M_1^{(m)}$, respectively, in each of which t detected myoelectric potentials are arranged in a chronological order as its elements and all the selected first correlated myoelectric signals are represented by a first myoelectric-potential matrix $M_1$ in which these row vectors are vertically arranged, a first muscular-synergic matrix $W_1$ in which n unit column vectors $W_1^{(1)}, W_1^{(2)}, \ldots,$ and $W_1^{(n)}$ each of which has m elements are horizontally arranged, a first control matrix $C_1$ in which n unit row vectors $C_1^{(1)}, C_1^{(2)}, \ldots,$ and $C_1^{(n)}$ each of which hast elements are vertically arranged, and a first error matrix $E_1$ so that these matrixes satisfy the below-shown relation through non-negative matrix factorization:

$$M_1 = W_1 C_1 + E_1,$$

calculates, when m selected second correlated myoelectric signals are represented by row vectors $M_2^{(1)}, M_2^{(2)}, \ldots,$ and $M_2^{(m)}$, respectively, in each of which t detected myoelectric potentials are arranged in a chronological order as its elements and all the selected second correlated myoelectric signals are represented by a second myoelectric-potential matrix $M_2$ in which these row vectors are vertically arranged, a second muscular-synergic matrix $W_2$ in which n unit column vectors $W_2^{(1)}, W_2^{(2)}, \ldots,$ and $W_2^{(n)}$ each of which has m elements are horizontally arranged, a second control matrix $C_2$ in which n unit row vectors $C_2^{(1)}, C_2^{(2)}, \ldots,$ and $C_2^{(n)}$ each of which hast elements are vertically arranged, and a second error matrix $E_2$ so that these matrixes satisfy the below-shown relation through non-negative matrix factorization:

$$M_2 = W_2 C_2 + E_2, \text{ and}$$

calculates the similarity by performing a predetermined similarity index calculation for the first and second muscular-synergic matrixes $W_1$ and $W_2$.

Since the first and second muscular-synergic matrixes $W_1$ and $W_2$, which represent a relation between mutually coordinated muscles, are used as a basis for similarity index calculation as described above, an evaluation value correctly reflecting the recovery level of the diseased part can be obtained.

A second exemplary aspect is a rehabilitation evaluation method for evaluating a level of recovery of a trainee by rehabilitation training, including: a myoelectric-signal acquisition step of acquiring a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs; a sensor signal acquisition step of acquiring a sensor signal output from a detection sensor, the detection sensor being configured to detect an amount of a change in the second-side part resulting from a comparative motion corresponding to a training motion performed in the first-side part in the rehabilitation training, in which the trainee is a detection target and performs the comparative motion in the second-side part; a selecting step of selecting, as a second correlated myoelectric signal, at least one second myoelectric signal having a correlation with the sensor signal acquired in the sensor signal acquisition step from among the plurality of second myoelectric signals acquired in the myoelectric-signal acquisition step; and a similarity outputting step of selecting, as a first correlated myoelectric signal, a first myoelectric signal that has been output from a first myoelectric sensor attached in a place that is left-right symmetric to a place of the second myoelectric sensor that has output the second correlated myoelectric signal selected in the selection step with respect to the limbs from among the plurality of first myoelectric signals acquired in the myoelectric-signal acquisition step, calculating a similarity between the first and second correlated myoelectric signals, and outputting the calculated similarity. Even in this embodiment, similarly to the first aspect, it is possible to accurately evaluate the recovery level of the diseased part and to reduce the overall time required for rehabilitation training.

A third exemplary aspect is a rehabilitation evaluation program for evaluating a level of recovery of a trainee by rehabilitation training, the rehabilitation evaluation program being adapted to cause a computer to perform: a myoelectric-signal acquisition step of acquiring a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs; a sensor signal acquisition step of acquiring a sensor signal output from a detection sensor, the detection sensor being configured to detect an amount of a change in the second-side part resulting from a comparative motion corresponding to a training motion performed in the first-side part in the rehabilitation training, in which the trainee is a detection target and performs the comparative motion in the second-side part; a selecting step of selecting, as a second correlated myoelectric signal, at least one second myoelectric signal having a correlation with the sensor signal acquired in the sensor signal acquisition step from among the plurality of second myoelectric signals acquired in the myoelectric-signal acquisition step; and a similarity outputting step of selecting, as a first correlated myoelectric signal, a first myoelectric signal that has been output from a first myoelectric sensor attached in a place that is left-right symmetric to a place of the second myoelectric sensor that has output the second correlated myoelectric signal selected in the selection step with respect to the limbs from among the plurality of first myoelectric signals acquired in the myoelectric-signal acquisition step, calculating a similarity between the first and second correlated myoelectric signals, and outputting the calculated similarity. Even in this embodiment, similarly to the first aspect, it is possible to accurately evaluate the recovery level of the diseased part and to reduce the overall time required for rehabilitation training.

According to the present disclosure, it is possible to provide a rehabilitation evaluation apparatus and the like capable of accurately evaluating the recovery level of a diseased part in a short time without requiring a troublesome trial-and-error process for adjusting positions of myoelectric-potential sensors every time a trainee does rehabilitation training.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

Figure 1:
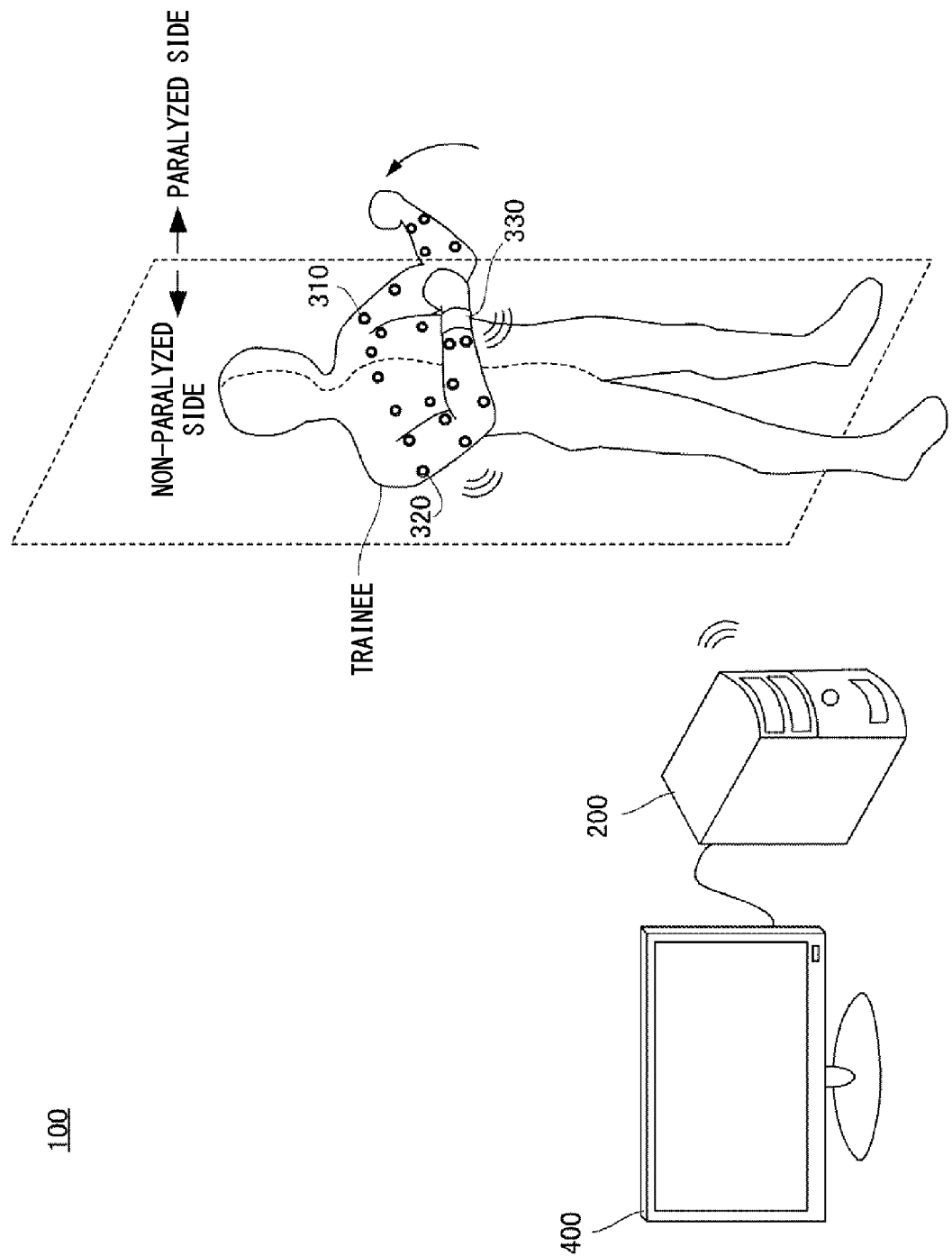
FIG. 1 is a schematic diagram showing an overall configuration of a rehabilitation training system according to the present disclosure.

FIG. 1 is a schematic diagram showing an overall configuration of a rehabilitation training system 100 according to an embodiment. The rehabilitation training system 100 is an apparatus that enables a trainee to do rehabilitation training. The trainee may be a patient who suffers from hemiplegia in which, when his/her limbs are divided into left and right sides on a center line connecting the center of the forehead and the crotch, a part on one of the sides is paralyzed. In this embodiment, as an example, a trainee is a patient whose left arm is paralyzed. As shown in the figure, the left half of trainee's body in which the left arm, which is the rehabilitation target, is located is referred to as a paralyzed side or a first side, and the right half of the body, i.e., the other side of the body is referred to as a non-paralyzed side or a second side.

The trainee performs, for example, a motion for raising his/her left forearm as a training motion in the rehabilitation training. A first myoelectric sensor 310 for measuring a myoelectric potential that changes as a result of this training motion is attached to each of a plurality of muscle parts on the paralyzed side. The first myoelectric sensor 310 is, for example, a sensor that performs surface electromyogram measurement (EMG measurement) and is able to output a first myoelectric signal, which is a measurement result, through wireless communication.

In this embodiment, the trainee also performs a comparative motion equivalent to the training motion on the non-paralyzed side. In the case where the trainee performs a motion for raising his/her left forearm as the training motion, he/she performs a motion for raising his/her right forearm as the comparative motion. A second myoelectric sensor 320 for measuring a myoelectric potential that changes as a result of this comparative motion is attached to each of a plurality of muscle parts on the non-paralyzed side. More specifically, each of the second myoelectric sensors 320 is attached in a place symmetric to a place of a respective one of the first myoelectric sensors 310 with respect to the center line of the limbs. The second myoelectric sensor 320 is identical to the first myoelectric sensor 310 and is able to output a second myoelectric signal, which is a measurement result, through wireless communication.

Further, an acceleration sensor 330 is also attached to the trainee as a detection sensor for detecting an amount of a change in the second-side part resulting from the comparative motion. In this example, since the trainee performs a motion for raising his/her right forearm as the comparative motion, the acceleration sensor 330 is attached in his/her right wrist in which a change in the motion is considerably large. The acceleration sensor 330 can detect an acceleration of the right wrist that changes during the comparative motion and is able to output an acceleration signal, which is a detection result, through wireless communication.

A PC (Personal Computer) 200, which is a computer that controls the whole rehabilitation training system 100, receives the first and second myoelectric signals and the acceleration signal, and calculates a recovery level of the paralyzed part. A result of the calculation and the like are displayed in a display 400. The display 400 includes, for example, a liquid-crystal panel as a display unit. The trainee and a training assistant or the like view the display in the display 400 and thereby are able to check a result (e.g., an outcome) of the rehabilitation training. Further, they can also check a training menu and the like in the display 400.

Figure 2:
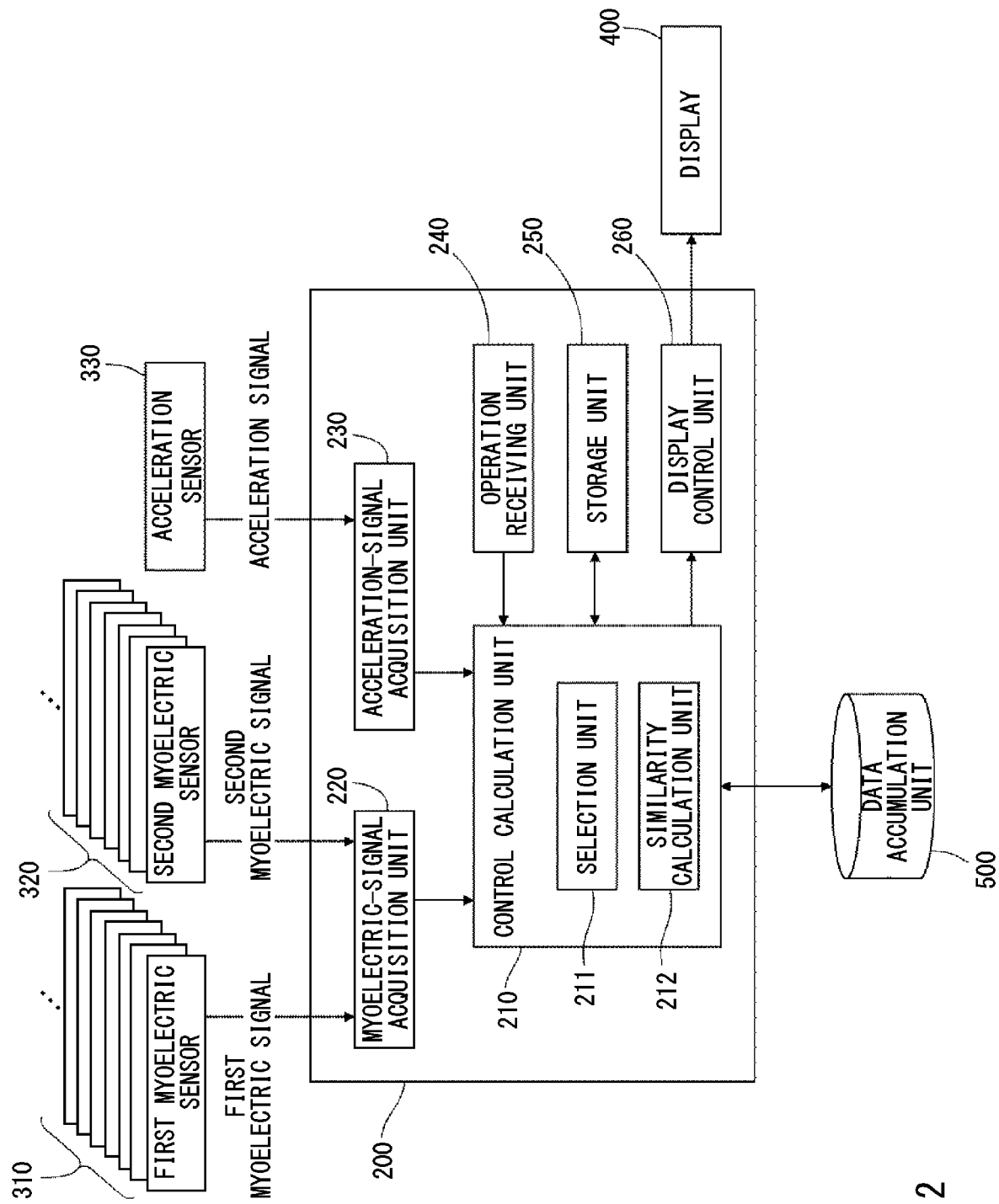
FIG. 2 is a block diagram of the whole rehabilitation training system.

FIG. 2 is a block diagram of the whole rehabilitation training system 100. The rehabilitation training system 100 includes the PC 200, the first myoelectric sensors 310, the second myoelectric sensors 320, the acceleration sensor 330, the display 400, and a data accumulation unit 500 connected to the PC 200 through a network.

Each of the first myoelectric sensors 310 measures a myoelectric potential of a muscle on the paralyzed-side and transmits a first myoelectric signal, which is its measurement result, to the PC 200. Each of the second myoelectric sensors 320 measures a myoelectric potential of a muscle on the non-paralyzed-side and transmits a second myoelectric signal, which is its measurement result, to the PC 200. The acceleration sensor 330 detects an acceleration and transmits an acceleration signal, which is its detection result, to the PC 200. Note that in this embodiment, although a wireless LAN is used as as example of communication means for each signal, the communication means is not limited to the wireless LAN. That is, the communication means may be any other type of wireless communication means or may be wired communication.

The PC 200 includes a myoelectric-signal acquisition unit 220 that functions as a receiving unit for receiving first and second myoelectric signals. The myoelectric-signal acquisition unit 220 may include a filter circuit for shaping a received myoelectric signal and, when the communication IF is an analog IF, an AD (Analog/Digital) conversion circuit or the like. Depending on the configuration, the myoelectric-signal acquisition unit 220 delivers the received first and second myoelectric signals, which have been subjected to the filtering process, to a control calculation unit 210.

The PC 200 includes an acceleration-signal acquisition unit 230 that functions as a receiving unit for receiving an acceleration signal. The acceleration-signal acquisition unit 230 may include a filter circuit for shaping a received acceleration signal and, when the communication IF is an analog IF, an AD conversion circuit or the like. Depending on the configuration, the acceleration-signal acquisition unit 230 delivers the received acceleration signal, which has been subjected to the filtering process, to the control calculation unit 210.

The PC 200 includes an operation receiving unit 240 that receives an instruction operation from the trainee or the training assistant. The operation receiving unit 240 receives, for example, a signal from a touch panel placed (e.g., layered) over the display 400, and signals from a connected mouse and a keyboard. The operation receiving unit 240 receives an instruction from the trainee or the training assistant, such as an instruction about a choice in a training menu and an instruction about completion of a preparation for starting training, and delivers the received instruction to the control calculation unit 210.

The PC 200 includes a storage unit 250 formed by, for example, an SSD (Solid State Drive). The storage unit 250 stores a control program for controlling the rehabilitation training system 100, and various parameter values, functions, look-up tables, etc. used for the control. Further, the storage unit 250 stores evaluation values representing similarities (i.e., degrees of similarities) and/or recovery levels, etc. (which will be described later).

The PC 200 includes a display control unit 260 that produces signals representing video images to be displayed and transmits the produced video signals to the display 400 connected to the PC 200. The control calculation unit 210 displays information, which is viewed by the trainee or the training assistant, in the display 400 in a viewable manner by using the display control unit 260.

The control calculation unit 210 is, for example, a CPU (Central Processing Unit) and controls the whole rehabilitation training system 100 in accordance with the control program. Further, the control calculation unit 210 also functions as a function calculation unit that performs various types of calculation related to the control. The selection unit 211 selects, as a second correlated myoelectric signal, at least one second myoelectric signal having a correlation with the acceleration signal acquired by the acceleration-signal acquisition unit 230 from among the second myoelectric signals acquired by the myoelectric-signal acquisition unit 220. Further, the similarity calculation unit 212 selects, as a first correlated myoelectric signal, a first myoelectric signal that has been output from the first myoelectric sensor 310 attached in a place that is left-right symmetric to a place of the second myoelectric sensor 320 that has output the second correlated myoelectric signal selected by the selection unit 211 with respect to the limbs from among the first myoelectric signals acquired by the myoelectric-signal acquisition unit 220. Then, the similarity calculation unit 212 calculates a similarity (i.e., a degree of a similarity) between the first and second correlated myoelectric signals. A specific calculation process for the above-described process will be explained later in detail.

The data accumulation unit 500 is, for example, a recording medium such as a hard disk drive connected to an intranet and accumulates similarities (i.e., degrees of similarities), evaluation values, etc. calculated by the control calculation unit 210. For example, a doctor can check a recovery level of a specific patient through a terminal or the like installed in his/her office by accessing the data accumulation unit 500 through the intranet. That is, information output from the similarity calculation unit 212 or the like may be output to the display 400 in a viewable manner or output to the data accumulation unit 500 for future use. In other words, by cooperating with the display control unit 260 and its interface for outputting a calculated similarity to the display 400, the similarity calculation unit 212 functions as a similarity output unit that outputs the calculated similarity in a viewable manner. Further, by cooperating with the interface for outputting the calculated similarity to the data accumulation unit 500, the similarity calculation unit 212 functions as a similarity output unit that outputs (and stores) the calculated similarity so that it can be used later. The similarity calculation unit 212 may also support other output means and can form other types of similarity output units by cooperating with hardware connected as appropriate. It should be noted that the PC 200 can acquire information on a trainee who starts training from now from the data accumulation unit 500.

Figure 3:
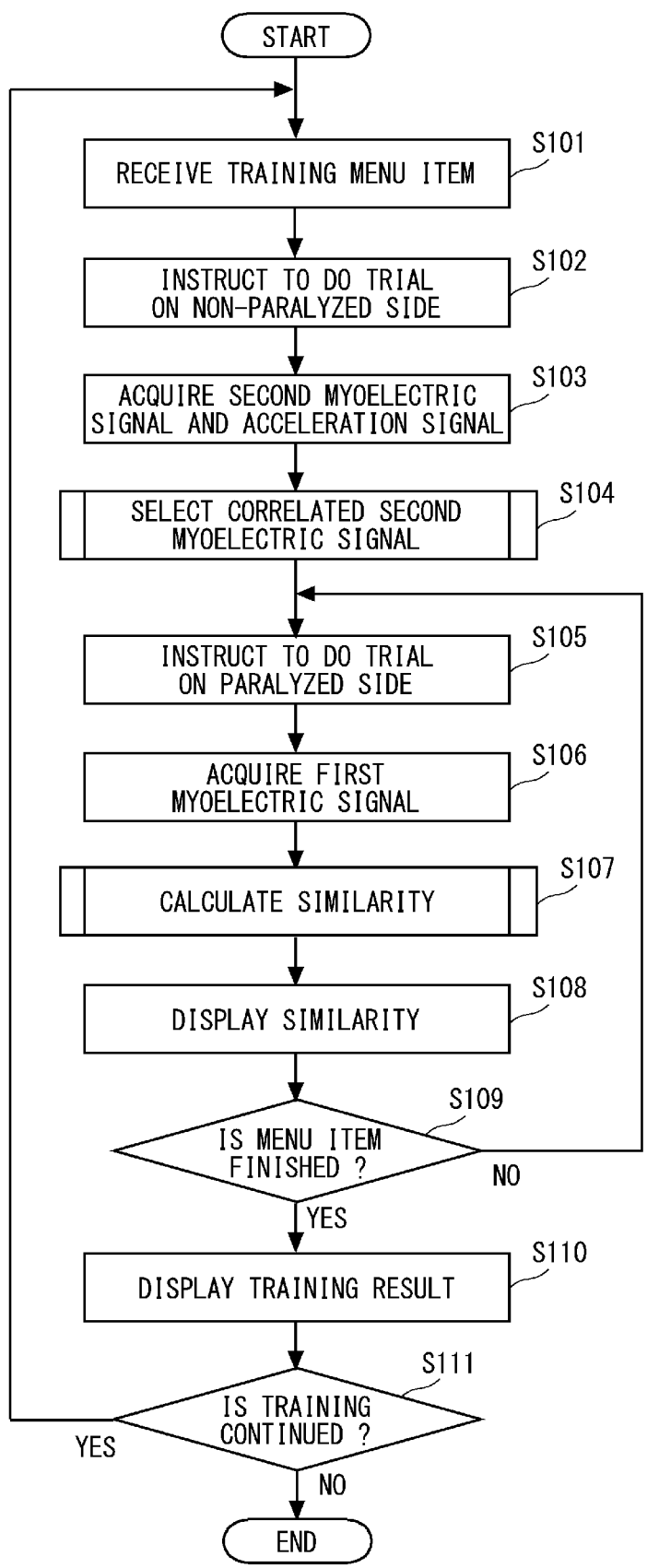
FIG. 3 is a flowchart showing a processing procedure of a control calculation unit.

Next, processes that are performed by the control calculation unit 210 when a trainee does a series of trainings are explained. FIG. 3 is a flowchart showing a procedure of processes performed by the control calculation unit 210. The flow is started in the following state. That is, each of the first myoelectric sensors 310 is attached in a predetermined place on a paralyzed side and each of the second myoelectric sensors 320 is attached in a place on a non-paralyzed side that is left-right symmetric to a place of a respective one of the first myoelectric sensors 310. Further, the acceleration sensor 330 is attached to the trainee's wrist on the non-paralyzed side.

In a step S101, the control calculation unit 210 receives a choice in a training menu from the trainee or the like through the operation receiving unit 240. The trainee or the like selects a training item that he/she will do from now in the training menu displayed in the display 400. Note that the trainee puts on (i.e., attaches) the first and second myoelectric sensors 310 and 320 and the acceleration sensor 330 in appropriate places in advance according to the training item to be selected in the training menu. In this example, it is assumed that the trainee selects a training item in the training menu in which the trainee repeats a training motion for raising his/her left forearm a plurality of times. Therefore, the first myoelectric sensors 310 are attached in the left upper body, which is located on the paralyzed side, in a scattered manner, and the second myoelectric sensors 320 are attached in the right upper body, which is located on the non-paralyzed side, in a scattered manner. Further, the acceleration sensor 330 is attached in the right wrist, which is located on the non-paralyzed side.

The control calculation unit 210 proceeds to a step S102, in which it instructs the trainee to try to perform a comparative motion on the non-paralyzed side through the display 400 or by using a voice-producing function. The comparative motion is a motion that corresponds to a training motion and is left-right symmetric thereto with respect to the limbs. In this example, since it is assumed that the trainee performs a motion for raising his/her left forearm as the training motion, the comparative motion is a motion for raising his/her right forearm. The trainee performs the comparative motion in accordance with the above-described trial instruction.

The control calculation unit 210 proceeds to a step S103, in which it acquires second myoelectric signals resulting from the comparative motion performed by the trainee by using the myoelectric-signal acquisition unit 220. Further, at the same time, the control calculation unit 210 acquires an acceleration signal resulting from the comparative motion by using the acceleration-signal acquisition unit 230. Then, the control calculation unit 210 proceeds to a step S104, in which the selection unit 211, which is a function calculation unit of the control calculation unit 210, selects, as a second correlated myoelectric signal(s), a second myoelectric signal(s) having a correlation with the acquired acceleration signal from among the acquired second myoelectric signals. The number of second myoelectric signals selected as second correlated myoelectric signals may be a fixed number determined in advance. Alternatively, the number may not be determined in advance and all the second myoelectric signals having a certain correlation level or larger may be selected. In any case, the number of the second correlated myoelectric signals is no smaller than one and no larger than the number of the second myoelectric signals. A specific calculation method or the like will be explained later in detail.

The control calculation unit 210 proceeds to a step S105, in which it instructs the trainee to try to perform a training motion on the paralyzed side through the display 400 or by using the voice-producing function. The trainee performs the training motion in accordance with this trial instruction. The control calculation unit 210 proceeds to a step S106, in which it acquires first myoelectric signals resulting from the training motion performed by the trainee by using the myoelectric-signal acquisition unit 220.

Then, the control calculation unit 210 proceeds to a step S107, in which the similarity calculation unit 212, which is a function calculation unit of the control calculation unit 210, selects, as a first correlated myoelectric signal(s), a first myoelectric signal(s) that has been output from a first myoelectric sensor 310 attached in a place that is left-right symmetric to a place of the second myoelectric sensor 320 that has output the second correlated myoelectric signal(s) selected by the selection unit 211 in the step S104 with respect to the limbs from among the acquired first myoelectric signals. Note that in this example, all the first myoelectric signals are acquired in the step S106 and then the first correlated myoelectric signal is selected in the step S107. However, only the first correlated myoelectric signal may be acquired from the first myoelectric sensor 310 that has been determined to be the target first myoelectric sensor 310 in the step S106. Further, the similarity calculation unit 212 calculates a similarity (i.e., a degree of a similarity) between the first and second correlated myoelectric signals. A specific calculation method or the like will be explained later in detail.

The control calculation unit 210 proceeds to a step S108, in which it displays the similarity calculated in the step S108 in the display 400 by using the display control unit 260. Then, the control calculation unit 210 proceeds to a step S109, in which it determines whether or not the training item has been finished, i.e., whether or not the number of trials of training motions has reached a predetermined number. When the number of trials has not reached the predetermined number, the control calculation unit 210 returns to the step S105 and the trainee repeats the training motion. Note that when the trainee repeatedly tries the training motion, the output of the first myoelectric sensor 310 that has been already selected in the step S107 may be continuously used as the first correlated myoelectric signal. By determining the first myoelectric sensor 310 that continuously outputs the first correlated myoelectric signal for the second and subsequent training motions, it is possible to enable the trainee to skip the troublesome task of performing the comparative motion every time the trainee performs the training motion. Further, since the common signal can be used as a signal to be compared in a repetition of the same trials, a change in the similarity calculated in each trial and statistical values such as an average value can also be used as indices indicating the recovery level.

When the number of trials has reached the predetermined number, the control calculation unit 210 proceeds to a step S110. In a step S110, the control calculation unit 210 displays a result of the series of trainings in the display 400 by using the display control unit 260. Further, the control calculation unit 210 outputs the result to the data accumulation unit 500. The data accumulation unit 500 receives the training result and stores it as information on the trainee who has performed the training. The control calculation unit 210 proceeds to a step S111, in which it determines whether or not an instruction to continue the training has been received from the trainee or the like through the operation receiving unit 240. When the control calculation unit 210 determines that the instruction for the continuation has been received, it returns to the step S101 and continues the series of training programs. When the control calculation unit 210 determines that the instruction for the continuation has not been received, it finishes the series of processes.

Figure 4:
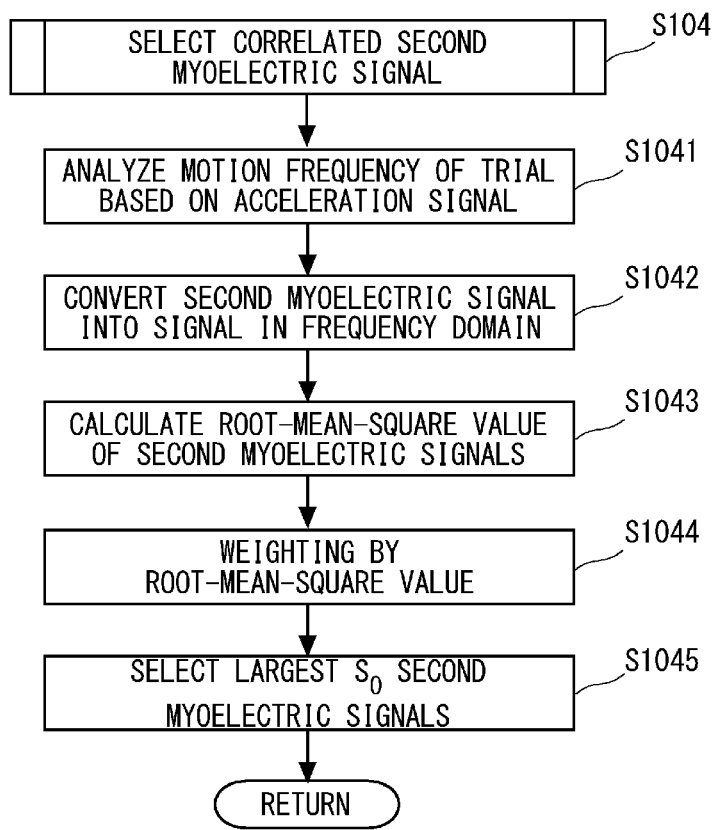
FIG. 4 is a flowchart showing a processing procedure of a selection unit.

Next, the process in the step S104 is explained in detail. FIG. 4 is a flowchart showing a detailed processing procedure in the step S104. In this embodiment, as described above, a first correlated myoelectric signal selected from a plurality of first myoelectric signals is compared with a second correlated myoelectric signal selected from a plurality of second myoelectric signals to calculate a similarity therebetween. That is, the similarity is not calculated by using all the myoelectric signals. Firstly, the meaning of this feature is explained.

It has become evident that when a trainee tries to do rehabilitation training, muscles that work for the trial and how much each muscle works in a coordinated manner differ from one individual to another and also differ according to the environment and the condition under which the trainee does the trial. Therefore, in the case were a recovery level on a paralyzed side is evaluated by comparing myoelectric signals that are generated as a result of a training motion and detected on the paralyzed side with those that are generated as a result of a comparative motion, which is an equivalent motion to the training motion, and detected on a non-paralyzed side, when the number of places at which myoelectric potentials are measured is small, the recovery level cannot be accurately evaluated. That is, there is a high possibility that a myoelectric signal of a muscle that considerably works for the comparative motion cannot be acquired and hence it is impossible to evaluate whether that muscle is properly working. It is conceivable to adjust the places at which myoelectric sensors are attached through a trial-and-error process. However, the task for this process is enormous and requires a long time. Therefore, the number of myoelectric sensors is increased so that myoelectric signals can be acquired at a large number of places at a time.

However, if comparisons are made by using all the myoelectric signals output from the larger number of attached myoelectric sensors, myoelectric signals from muscles that do not work much for the training motion become dominant. As a result, large values are always calculated (i.e., obtained) as similarities. That is, calculated values are not appropriate as values for evaluating the recovery level. Therefore, in this embodiment, a myoelectric signal output from a myoelectric sensor attached in a muscle that considerably works for a training motion as long as it is not paralyzed is selected from among myoelectric signals acquired from a large number of attached myoelectric sensors and used for the evaluation calculation.

Accordingly, firstly, a trainee tries to perform a comparative motion on a non-paralyzed side and a myoelectric signal output from a myoelectric sensor attached in a muscle that considerably works for the comparative motion is selected. Specifically, as a second correlated myoelectric signal, a second myoelectric signal that considerably reacts to the comparative motion is selected from among second myoelectric signals output from the second myoelectric sensors 320. However, each of the second myoelectric signals output from the second myoelectric sensors 320 could change with time. Therefore, it is impossible to determine which of the second myoelectric signals reacts to the comparative motion just by comparing these second myoelectric signals with each other. Therefore, in this embodiment, an acceleration sensor 330 is used as a sensor that detects an amount of a physical change in a part that moves as a result of the comparative motion. That is, among the second myoelectric signals, one having a large correlation with an acceleration signal, which is an output of the acceleration sensor 330, is regarded as a signal from a muscle that considerably reacts to the comparative motion. The second myoelectric signal selected in this manner is defined as a second correlated myoelectric signal. A processing procedure explained below is an example of a procedure for selecting a second correlated myoelectric signal.

In a step S1041, the selection unit 211 analyzes (i.e., obtains) a motion frequency of a motion for raising the right forearm, which is the comparative motion, based on the acceleration signal. Specifically, a Fourier transform is performed on the acceleration signal and a frequency at which the acceleration signal has the maximum strength is determined as the motion frequency. The selection unit 211 proceeds to a step S1042, in which it converts each of the second myoelectric signals into a signal in a frequency domain by performing a Fourier transform and extracts a strength of each signal at the motion frequency analyzed (i.e., obtained) in the step S1041.

The selection unit 211 proceeds to a step S1043, in which it calculates a root-mean-square value for each of the second myoelectric signals for which the Fourier transform has not been performed yet. Specifically, when first to t-th individual signal values b of a P-th second myoelectric signal $M_2^{(p)}$ are expressed in the order of sampling as follows:

$$M_2^{(p)} = (b_{p1}, b_{p2}, b_{p3}, \ldots, b_{pt}) \quad \text{[Expression 1]}$$

a root-mean-square value $R^{(p)}$ of the second myoelectric signal $M_2^{(p)}$ is calculated as follows:

$$R^{(p)} = \sqrt{\frac{1}{t} \sum_{i=1}^{t} b_{pi}} \quad \text{[Expression 2]}$$

The selection unit 211 proceeds to a step S1044, in which it calculates calculated comparison values that are obtained by adding second myoelectric signal root-mean-square values calculated in the step S1043 to strengths of respective second myoelectric signals extracted in the step S1042 and thereby assigning weights to them. For example, when a strength of a P-th second myoelectric signal $M_2^{(p)}$ at the motion frequency is $F^{(p)}$, a calculated comparison value $Q^{(p)}$ of this second myoelectric signal $M_2^{(p)}$ is expressed as follows:

$$Q^{(p)} = F^{(p)} + R^{(p)} \quad \text{[Expression 3]}$$

The selection unit 211 proceeds to a step S1045, in which it selects largest $S_0$ calculated comparison values of the second myoelectric signals and defines the second myoelectric signals corresponding to the selected comparison values as second correlated myoelectric signals. For example, in the case where nine second myoelectric sensors 320 are attached in the second-side part, the number of second myoelectric signals is nine. Further, when the number $S_0$ is set to five ($S_0$=5), five second correlated myoelectric signals are determined. Through the above-described series of processes, second correlated myoelectric signals are selected. Note that the selection unit 211 may define a reference calculated comparison value $Q_0$ in advance. Then, the selection unit 211 may determine all the second myoelectric signals whose calculated comparison values are equal to or larger than this value as second correlated myoelectric signals. In this case, the number of second correlated myoelectric signals changes every time second correlated myoelectric signals are determined.

Figure 5:
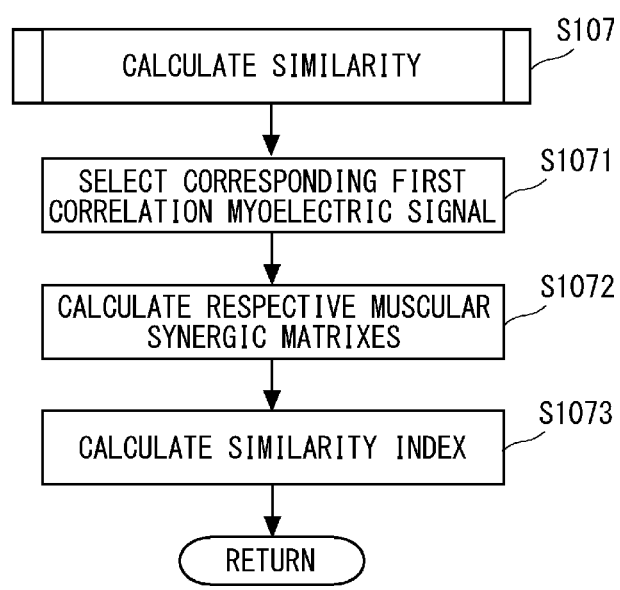
FIG. 5 is a flowchart showing a processing procedure of a similarity calculation unit.

Next, the process in the step S107 is explained in detail. FIG. 5 is a flowchart showing a detailed processing procedure in the step S107. In a step S1071, the similarity calculation unit 212 selects corresponding first correlated myoelectric signals from among the first myoelectric signals acquired in the step S106. For example, when five second correlated myoelectric signals are selected in the step S107, the number of first correlated myoelectric signals selected in this process is also five.

The similarity calculation unit 212 proceeds to a step S1072, in which it calculates respective muscular-synergic matrixes for the first correlated myoelectric signals. In the case where m first correlated myoelectric signals are selected in the step S1071, when each of first to m-th first correlated myoelectric signals is expressed by a row vector in which first to t-th signal values a of individual myoelectric potentials are arranged in the order of sampling, i.e., in a chronological order, it is expressed as follows:

$$M_1^{(1)} = (a_{11}, a_{12}, a_{13}, \ldots, a_{1t})$$
$$M_1^{(2)} = (a_{21}, a_{22}, a_{23}, \ldots, a_{2t})$$
$$\vdots$$
$$M_1^{(m)} = (a_{m1}, a_{m2}, a_{m3}, \ldots, a_{mt}) \quad \text{[Expression 4]}$$

When a matrix which represents all the first correlated myoelectric signals, and in which row vectors representing respective first correlated myoelectric signals are vertically arranged is represented by a first myoelectric-potential matrix $M_1$, it is expressed as follows:

$$M_1 = \begin{pmatrix} M_1^{(1)} \\ M_1^{(2)} \\ \vdots \\ M_1^{(m)} \end{pmatrix} = \begin{pmatrix} a_{11} & a_{12} & a_{13} & \cdots & a_{1t} \\ a_{21} & a_{22} & a_{23} & \cdots & a_{2t} \\ \vdots & \vdots & \vdots & \ddots & \vdots \\ a_{m1} & a_{m2} & a_{m3} & \cdots & a_{mt} \end{pmatrix} \qquad \text{[Expression 5]}$$

This first myoelectric-potential matrix $M_1$ is factorized by using non-negative matrix factorization as follows:

$$M_1 = W_1 C_1 + E_1 \qquad \text{[Expression 6]}$$

In the expression, $W_1$ is a first muscular-synergic matrix. The first muscular-synergic matrix $W_1$ is a matrix in which first to n-th unit column vectors $W_1^{(1)}, W_1^{(2)}, \ldots,$ and $W_1^{(n)}$ each of which including m elements, i.e., first to m-th elements j as expressed as follows:

$$W_1^{(1)} = \begin{pmatrix} j_{11} \\ j_{21} \\ j_{31} \\ \vdots \\ j_{m1} \end{pmatrix} \qquad \text{[Expression 7]}$$

$$W_1^{(2)} = \begin{pmatrix} j_{12} \\ j_{22} \\ j_{32} \\ \vdots \\ j_{m2} \end{pmatrix}$$

$$\vdots$$

$$W_1^{(n)} = \begin{pmatrix} j_{1n} \\ j_{2n} \\ j_{3n} \\ \vdots \\ j_{mn} \end{pmatrix}$$

are horizontally arranged as follows:

$$W_1 = \begin{pmatrix} W_1^{(1)} & W_1^{(2)} & \cdots & W_1^{(n)} \end{pmatrix} = \qquad \text{[Expression 8]}$$

$$\begin{pmatrix} j_{11} & j_{12} & j_{13} & \cdots & j_{1n} \\ j_{21} & j_{22} & j_{23} & \cdots & j_{2n} \\ \vdots & \vdots & \vdots & \ddots & \vdots \\ j_{m1} & j_{m2} & j_{m3} & \cdots & j_{mn} \end{pmatrix}$$

Further, $C_1$ is a first control matrix. The first control matrix $C_1$ is a matrix in which first to n-th row vectors $C_1^{(1)}, C_1^{(2)}, \ldots,$ and $C_1^{(n)}$ each of which including t elements, i.e., first to t-th elements g as expressed as follows:

$$C_1^{(1)} = (g_{11}, g_{12}, g_{13}, \ldots, g_{1t}) \qquad \text{[Expression 9]}$$
$$C_1^{(2)} = (g_{21}, g_{22}, g_{23}, \ldots, g_{2t})$$
$$\vdots$$
$$C_1^{(n)} = (g_{n1}, g_{n2}, g_{n3}, \ldots, g_{nt})$$

are vertically arranged as follows:

$$C_1 = \begin{pmatrix} C_1^{(1)} \\ C_1^{(2)} \\ \vdots \\ C_1^{(n)} \end{pmatrix} = \begin{pmatrix} g_{11} & g_{12} & g_{13} & \cdots & g_{1t} \\ g_{21} & g_{22} & g_{23} & \cdots & g_{2t} \\ \vdots & \vdots & \vdots & \ddots & \vdots \\ g_{n1} & g_{n2} & g_{n3} & \cdots & g_{nt} \end{pmatrix} \qquad \text{[Expression 10]}$$

Further, $E_1$ is an error matrix. Similarly to the first myoelectric-potential matrix $M_1$, the error matrix $E_1$ includes m×t elements.

Similarly to the above-described process, similar calculation is performed for second correlated myoelectric signals. When each of first to m-th second correlated myoelectric signals is expressed by a row vector in which first to t-th signal values b of individual myoelectric potentials are arranged in the order of sampling, i.e., in a chronological order, it is expressed as follows:

$$M_2^{(1)} = (b_{11}, b_{12}, b_{13}, \ldots, b_{1t}) \qquad \text{[Expression 11]}$$
$$M_2^{(2)} = (b_{21}, b_{22}, b_{23}, \ldots, b_{2t})$$
$$\vdots$$
$$M_2^{(m)} = (b_{m1}, b_{m2}, b_{m3}, \ldots, b_{mt})$$

When a matrix which represents all the second correlated myoelectric signals, and in which row vectors representing respective second correlated myoelectric signals are vertically arranged is represented by a second myoelectric-potential matrix $M_2$, it is expressed as follows:

$$M_2 = \begin{pmatrix} M_2^{(1)} \\ M_2^{(2)} \\ \vdots \\ M_2^{(m)} \end{pmatrix} = \begin{pmatrix} b_{11} & b_{12} & b_{13} & \cdots & b_{1t} \\ b_{21} & b_{22} & b_{23} & \cdots & b_{2t} \\ \vdots & \vdots & \vdots & \ddots & \vdots \\ b_{m1} & b_{m2} & b_{m3} & \cdots & b_{mt} \end{pmatrix} \qquad \text{[Expression 12]}$$

This second myoelectric-potential matrix $M_2$ is factorized by using non-negative matrix factorization as follows:

$$M_2 = W_2 C_2 + E_2 \qquad \text{[Expression 13]}$$

In the expression, $W_2$ is a second muscular-synergic matrix. The second muscular-synergic matrix $W_2$ is a matrix in which first to n-th unit column vectors $W_2^{(1)}, W_2^{(2)}, \ldots,$ and $W_2^{(n)}$ each of which including m elements, i.e., first to m-th elements k as expressed as follows:

$$W_2^{(1)} = \begin{pmatrix} k_{11} \\ k_{21} \\ k_{31} \\ \vdots \\ k_{m1} \end{pmatrix}$$

$$W_2^{(2)} = \begin{pmatrix} k_{12} \\ k_{22} \\ k_{32} \\ \vdots \\ k_{m2} \end{pmatrix}$$

$$\vdots$$

$$W_2^{(n)} = \begin{pmatrix} k_{1n} \\ k_{2n} \\ k_{3n} \\ \vdots \\ k_{mn} \end{pmatrix}$$

[Expression 14]

are horizontally arranged as follows:

$$W_2 = (W_2^{(1)} \quad W_2^{(2)} \quad \ldots \quad W_2^{(n)}) = \begin{pmatrix} k_{11} & k_{12} & k_{13} & \ldots & k_{1n} \\ k_{21} & k_{22} & k_{23} & \ldots & k_{2n} \\ \vdots & \vdots & \vdots & \ddots & \vdots \\ k_{m1} & k_{m2} & k_{m3} & \ldots & k_{mn} \end{pmatrix}$$

[Expression 15]

Further, $C_2$ is a second control matrix. The second control matrix $C_2$ is a matrix in which first to n-th row vectors $C_2^{(1)}$, $C_2^{(2)}$, ..., and $C_2^{(n)}$ each of which including t elements, i.e., first to t-th elements h as expressed as follows:

$$C_2^{(1)} = (h_{11}, h_{12}, h_{13}, \ldots, h_{1t})$$
$$C_2^{(2)} = (h_{21}, h_{22}, h_{23}, \ldots, h_{2t})$$
$$\vdots$$
$$C_2^{(n)} = (h_{n1}, h_{n2}, h_{n3}, \ldots, h_{nt})$$

[Expression 16]

are vertically arranged as follows:

$$C_2 = \begin{pmatrix} C_2^{(1)} \\ C_2^{(2)} \\ \vdots \\ C_2^{(n)} \end{pmatrix} = \begin{pmatrix} h_{11} & h_{12} & h_{13} & \ldots & h_{1t} \\ h_{21} & h_{22} & h_{23} & \ldots & h_{2t} \\ \vdots & \vdots & \vdots & \ddots & \vdots \\ h_{n1} & h_{n2} & h_{n3} & \ldots & h_{nt} \end{pmatrix}$$

[Expression 17]

Further, $E_2$ is an error matrix. Similarly to the second myoelectric-potential matrix $M_2$, the error matrix $E_2$ includes m×t elements. Note that the above-described calculation is explained in detail in, for example, Japanese Unexamined Patent Application Publication No. 2015-73805 which was filed by the applicant of the present application.

After the first and second muscular-synergic matrixes $W_1$ and $W_2$ are calculated as described above, the similarity calculation unit 212 proceeds to a step S1073, in which it calculates a similarity (i.e., a degree of a similarity) by performing similarity index calculation using these matrixes. A similarity SI is calculated by the following expression.

$$SI = \frac{1}{n} \sum_{i=1}^{n} (r(W_1^{(i)}, W_2^{(i)}))$$

[Expression 18]

In the expression, $W_1^{(i)}$ is an i-th unit column vector of the first muscular-synergic matrix $W_1$ and $W_2^{(i)}$ is an i-th unit column vector of the second muscular-synergic matrix $W_2$. The number n is the number of unit column vectors in each matrix as described above. Further, $r(W_1^{(i)}, W_2^{(i)})$ represents a Pearson's correlation coefficient in an i-th unit column vector and expressed as follows:

$$r(W_1^{(i)}, W_2^{(i)}) = \frac{\sum_{l=1}^{m}(j_{li} - \bar{j}_i)(k_{li} - \bar{k}_i)}{m S_{ji} S_{ki}}$$

[Expression 19]

In the expression, m is the number of elements in each unit column vector as described above. Further, $$\bar{j}_i, \bar{k}_i, S_{ji}, S_{ki}$$

[Expression 20]

are an average value of elements of $W_1^{(i)}$, an average value of elements of $W_2^{(i)}$, a standard deviation of elements of $W_1^{(i)}$, and a standard deviation of elements of $W_2^{(i)}$, respectively. The similarity SI calculated in this way takes a value between zero and one. Further, the closer the similarity SI is to one, the more the muscular-synergic matrixes resemble each other. That is, it indicates that muscular activities on the paralyzed and non-paralyzed sides resemble each other. Through the above-described series of processes, the similarity is calculated.

Figure 6:
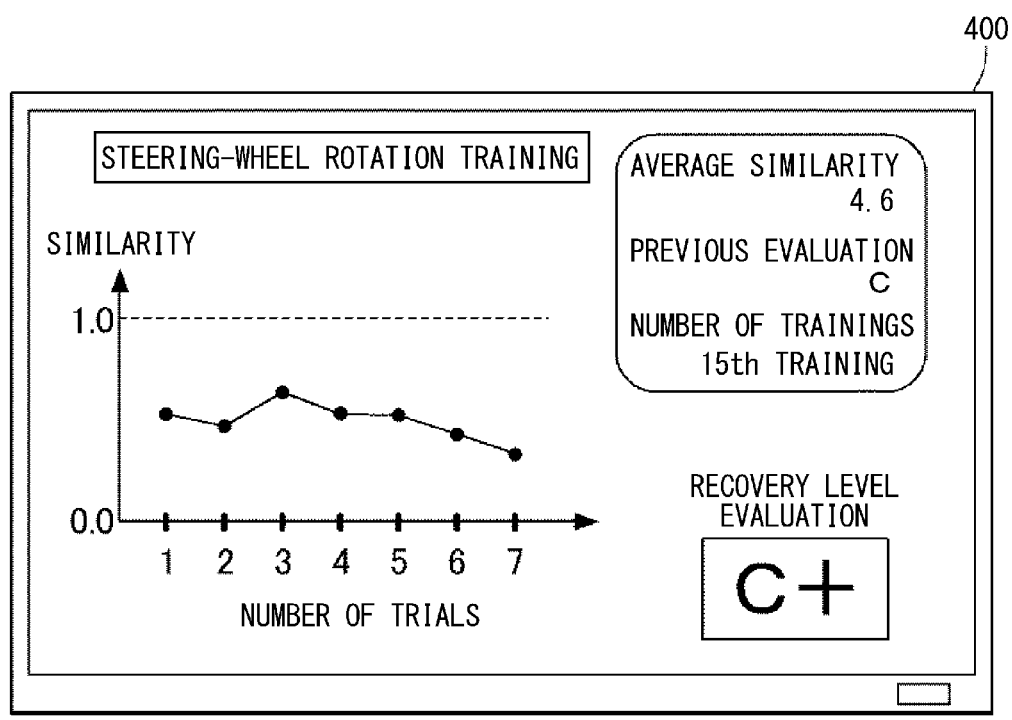
FIG. 6 is an example of a display screen showing the recovery level.

FIG. 6 is an example of a display screen (i.e., displayed image) showing a recovery level of a trainee displayed in the display 400. As shown in the figure, similarities each of which is calculated every time the trainee tries a training motion are plotted in a graph and they are expressed by a line graph. That is, an overall evaluation for a series of trainings is shown as a recovery-level evaluation. The recovery-level evaluation is determined by using a plurality of calculated similarities. For example, an average value of similarities is calculated and an evaluation corresponding to the calculated average value ("C+" in the example in the figure) is obtained. As shown in the figure, a training name and a past training history may be added as displayed items in the display screen.

In the above-described embodiment, a motion for raising a forearm is used as an example of a training motion. However, needless to say, other types of motions may be used. For example, a steering wheel may be prepared and a trainee may rotate it as a training motion. In this case, when the trainee rotates the steering wheel with both hands, a rotating motion in a clockwise direction is symmetric to a rotating motion in a counterclockwise direction. Therefore, one of these motions can be used as a training motion and the other motion can be used as a comparative motion. In this way, it is possible to acquire myoelectric signals on a paralyzed side and those on a non-paralyzed side in a continuous manner.

Further, the paralyzed part is not limited to the upper body and it may be a lower body. For example, in the case where a patient with an impaired right leg performs rehabilitation training, it is possible to apply the above-described technique for walking motions in which the patient alternately moves the right leg on the paralyzed side and the left leg on the non-paralyzed side on a treadmill, and thereby to evaluate the recovery level of the right leg. A control program for controlling the rehabilitation training system 100 may be configured so that a trainee or the like can perform various training programs by selecting corresponding items.

Further, although the acceleration sensor 330 is used in the above-described embodiment, the detection sensor for detecting an amount of a physical change resulting from a comparative motion is not limited the acceleration sensor. Sensors that can be directly attached to the moving part as in the case of the acceleration sensor are preferred. However, use of non-contact-type sensors can reduce the time necessary for attaching the sensors and the inconvenience in the training. For example, it is possible to use a digital camera as a non-contact-type sensor. By taking images of a moving part by a camera disposed by the side thereof and analyzing changes in the moving part on the taken images, it is possible to detect an amount of a physical change in the moving part and thereby calculate a motion frequency of the comparative motion. Further, the detection sensor is not limited to those that directly detect an amount of a physical change in a moving part resulting from the comparative motion. For example, the physical position of the moving part during the comparative motion may be detected in a time-series manner. Then, an amount of a change in the moving part may be calculated and detected by processing the time-series data on the position.

Further, in the above-described embodiment, when the selection unit 211 selects a second correlated myoelectric signal, it calculates a calculated comparison value by adding a root-mean-square value calculated from a sampled value of a target second myoelectric signal that has been already subjected to a filtering process to a strength at a motion frequency. However, to simplify the calculation, the addition of the root-mean-square value may be skipped. Needless to say, the accuracy of the evaluation may be improved by incorporating other factors. Further, in the above-described embodiment, the selection unit 211 selects a second correlated myoelectric signal based on the motion frequency of the comparative motion. However, the second correlated myoelectric signal may be selected based on other physical quantities.

Further, although the calculation of similarities uses a Pearson's correlation coefficient in the above-described embodiment, it is possible to use other evaluation formulas. Any publicly-known evaluation formula can be used, provided that it can be used to evaluate a similarity between first and second muscular-synergic matrixes $W_1$ and $W_2$.

Further, the order according to which processes in the above-described flow are performed is not specifically specified. That is, they may be performed in an arbitrary order as long as an output in a proceeding process is not used in a subsequent process. In the above explanations, terms "firstly", "next", etc. are used. However, these terms do not means that processes have to be performed according to the literal meanings of these terms.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A rehabilitation evaluation apparatus configured to evaluate a level of recovery of a trainee by rehabilitation training, comprising:

a processor configured to:

acquire a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs;

acquire a sensor signal output from a detection sensor attached to the trainee on the second-side part, the detection sensor being configured to detect an amount of a change in the motion of the second-side part resulting from a comparative motion corresponding to a training motion performed in the first-side part in the rehabilitation training, in which the trainee is a detection target and performs the comparative motion in the second-side part;

select, as a second correlated myoelectric signal, at least one second myoelectric signal from among the plurality of second myoelectric signals having a correlation with the sensor signal greater than a predetermined correlation, including:

determine a motion frequency of the comparative motion from the sensor signal, the motion frequency being a frequency at which the sensor signal has a maximum strength, and select a myoelectric signal having a predetermined strength or stronger at the motion frequency from among the plurality of second myoelectric signals as the second correlated myoelectric signal having the correlation with the sensor signal greater than the predetermined correlation;

select, as a first correlated myoelectric signal, a first myoelectric signal that has been output from a first myoelectric sensor attached in a place that is left-right symmetric to a place of the second myoelectric sensor that has output the second correlated myoelectric signal with respect to the limbs from among the plurality of first myoelectric signals;

calculate a similarity between the first and second correlated myoelectric signals; and output the calculated similarity, wherein in the selection of the second correlated myoelectric signal, the at least one second myoelectric signal is selected based on the correlation between the sensor signal output by the detection sensor attached in a place where an acceleration changes according to the comparative motion and the second myoelectric signals output by the second myoelectric sensors for measuring a myoelectric potential that changes as a result of the comparative motion, and in selecting the second correlated myoelectric signal, the processor is configured to:
add a root-mean-square value calculated from each of the plurality of second myoelectric signals to the predetermined strength or stronger of the myoelectric signal selected from among the plurality of second myoelectric signals,
compare a resultant value of the addition with a predetermined value, and
select the myoelectric signal selected from among the plurality of second myoelectric signals as the second correlated myoelectric signal when the resultant value is equal to or larger than the predetermined value.

2. The rehabilitation evaluation apparatus according to claim 1, wherein when the trainee tries to perform the training motion repeatedly, the processor is configured to continuously use an output of the first myoelectric sensor that has output the first correlated myoelectric signal selected once as the first correlated myoelectric signal.

3. The rehabilitation evaluation apparatus according to claim 1, wherein the processor is configured to, in selecting the second correlated myoelectric signal:
add a root-mean-square value calculated from sampled values obtained after a filtering process is performed for a target second myoelectric signal to the predetermined strength at the motion frequency, and
compare a resultant value of the addition with a predetermined value.

4. The rehabilitation evaluation apparatus according to claim 1, wherein the processor is configured to:
calculate,
when m selected first correlated myoelectric signals are represented by row vectors $M_1^{(1)}, M_1^{(2)}, \ldots,$ and $M_1^{(m)}$, respectively, in each of which t detected myoelectric potentials are arranged in a chronological order as its elements and all the selected first correlated myoelectric signals are represented by a first myoelectric-potential matrix $M_1$ in which these row vectors are vertically arranged,
a first muscular-synergic matrix $W_1$ in which n unit column vectors $W_1^{(1)}, W_1^{(2)}, \ldots,$ and $W_1^{(n)}$ each of which has m elements are horizontally arranged, a first control matrix $C_1$ in which n unit row vectors $C_1^{(1)}, C_1^{(2)}, \ldots,$ and $C_1^{(n)}$ each of which has t elements are vertically arranged, and a first error matrix $E_1$ so that these matrixes satisfy the below-shown relation through non-negative matrix factorization:

$$M_1 = W_1 C_1 + E_1,$$

calculate,
when m selected second correlated myoelectric signals are represented by row vectors $M_2^{(1)}, M_2^{(2)}, \ldots,$ and $M_2^{(m)}$, respectively, in each of which t detected myoelectric potentials are arranged in a chronological order as its elements and all the selected second correlated myoelectric signals are represented by a second myoelectric-potential matrix $M_2$ in which these row vectors are vertically arranged,
a second muscular-synergic matrix $W_2$ in which n unit column vectors $W_2^{(1)}, W_2^{(2)}, \ldots,$ and $W_2^{(n)}$ each of which has m elements are horizontally arranged, a second control matrix $C_2$ in which n unit row vectors $C_2^{(1)}, C_2^{(2)}, \ldots,$ and $C_2^{(n)}$ each of which has t elements are vertically arranged, and a second error matrix $E_2$ so that these matrixes satisfy the below-shown relation through non-negative matrix factorization:

$$M_2 = W_2 C_2 + E_2, \text{ and}$$

calculate the similarity by performing a predetermined similarity index calculation for the first and second muscular-synergic matrixes $W_1$ and $W_2$.

5. The rehabilitation evaluation apparatus according to claim 4, wherein the processor is configured to, in performing the predetermined similarity index calculation, use a Pearson's correlation coefficient.

6. The rehabilitation evaluation apparatus according to claim 4, wherein the processor is configured to, in performing the predetermined similarity index calculation, calculate the similarity as SI, where:

$$SI = \frac{1}{n}\sum_{i=1}^{n}\left(r\left(W_1^{(i)}, W_2^{(i)}\right)\right),$$

$W_1^{(i)}$ is an i-th unit column vector of the first muscular-synergic matrix $W_1$,
$W_2^{(i)}$ is an i-th unit column vector of the second muscular-synergic matrix $W_2$,
$r(W_1^{(i)}, W_2^{(i)})$ represents a Pearson's correlation coefficient in an i-th unit column vector expressed as:

$$r\left(W_1^{(i)}, W_2^{(i)}\right) = \frac{\sum_{l=1}^{m}(j_{li} - \bar{j}_i)(k_{li} - \bar{k}_i)}{mS_{ji}S_{ki}},$$

and
$\bar{j}_i, \bar{k}_i, S_{ji}, S_{ki}$ are an average value of elements of $W_1^{(i)}$, an average value of elements of $W_2^{(i)}$, a standard deviation of elements of $W_1^{(i)}$, and a standard deviation of elements of $W_2^{(i)}$, respectively.

7. The rehabilitation evaluation apparatus according to claim 1, wherein a number of the at least one second myoelectric signal selected as the second correlated myoelectric signal changes from a first selection of the second correlated myoelectric signal to a second selection of the second correlated myoelectric signal.

8. The rehabilitation evaluation apparatus according to claim 1, wherein a number of the at least one second myoelectric signal first selected as the second correlated myoelectric signal is less than a total number of the plurality of second myoelectric signals.

9. The rehabilitation evaluation apparatus according to claim 1, wherein processor is configured to:
calculate the root-mean-square value from the plurality of second myoelectric signals before a Fourier transform has been performed on the plurality of second myoelectric signals, and
select the myoelectric signal having the predetermined strength or stronger at the motion frequency from among the plurality of second myoelectric signals, having the Fourier transform performed thereon, as the second correlated myoelectric signal having the correlation with the sensor signal greater than the predetermined correlation.

10. A rehabilitation evaluation method for evaluating a level of recovery of a trainee by rehabilitation training, comprising:
acquiring a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs;
acquiring a sensor signal output from a detection sensor attached to the trainee on the second-side part, the detection sensor being configured to detect an amount of a change in the motion of the second-side part resulting from a comparative motion corresponding to a training motion performed in the first-side part in the rehabilitation training, in which the trainee is a detection target and performs the comparative motion in the second-side part;
selecting, as a second correlated myoelectric signal, at least one second myoelectric signal from among the plurality of second myoelectric signals having a correlation with the sensor signal greater than a predetermined correlation, including:
determining a motion frequency of the comparative motion from the sensor signal, the motion frequency being a frequency at which the sensor signal has a maximum strength, and
selecting a myoelectric signal having a predetermined strength or stronger at the motion frequency from among the plurality of second myoelectric signals as the second correlated myoelectric signal having the correlation with the sensor signal greater than the predetermined correlation;
selecting, as a first correlated myoelectric signal, a first myoelectric signal that has been output from a first myoelectric sensor attached in a place that is left-right symmetric to a place of the second myoelectric sensor that has output the second correlated myoelectric signal with respect to the limbs from among the plurality of first myoelectric signals;
calculating a similarity between the first and second correlated myoelectric signals; and
outputting the calculated similarity, wherein
in the selecting of the second correlated myoelectric signal, the at least one second myoelectric signal is selected based on the correlation between the sensor signal output by the detection sensor attached in a place where an acceleration changes according to the comparative motion and the second myoelectric signals output by the second myoelectric sensors for measuring a myoelectric potential that changes as a result of the comparative motion, and
selecting the second correlated myoelectric signal includes:

adding a root-mean-square value calculated from each of the plurality of second myoelectric signals to the predetermined strength or stronger of the myoelectric signal selected from among the plurality of second myoelectric signals,
comparing a resultant value of the addition with a predetermined value, and
selecting the myoelectric signal selected from among the plurality of second myoelectric signals as the second correlated myoelectric signal when the resultant value is equal to or larger than the predetermined value.

11. A non-transitory computer readable medium storing a rehabilitation evaluation program for evaluating a level of recovery of a trainee by rehabilitation training, the rehabilitation evaluation program being adapted to cause a computer to perform:
acquiring a plurality of first myoelectric signals output from respective first myoelectric sensors attached in a plurality of places on a first-side part and a plurality of second myoelectric signals output from respective second myoelectric sensors attached in a plurality of places on a second-side part, the first-side part being located, when limbs of the trainee are divided into left and right sides, on one of the sides in which a rehabilitation-target part is included, the second-side part being located on the other of the sides in which the rehabilitation-target part is not included, the places of the second myoelectric sensors being left-right symmetric to the places of respective first myoelectric sensors with respect to the limbs;
acquiring a sensor signal output from a detection sensor attached to the trainee on the second-side part, the detection sensor being configured to detect an amount of a change in the motion of the second-side part resulting from a comparative motion corresponding to a training motion performed in the first-side part in the rehabilitation training, in which the trainee is a detection target and performs the comparative motion in the second-side part;
selecting, as a second correlated myoelectric signal, at least one second myoelectric signal from among the plurality of second myoelectric signals having a correlation with the sensor signal greater than a predetermined correlation, including:
determining a motion frequency of the comparative motion from the sensor signal, the motion frequency being a frequency at which the sensor signal has a maximum strength, and
selecting a myoelectric signal having a predetermined strength or stronger at the motion frequency from among the plurality of second myoelectric signals as the second correlated myoelectric signal having the correlation with the sensor signal greater than the predetermined correlation;
selecting, as a first correlated myoelectric signal, a first myoelectric signal that has been output from a first myoelectric sensor attached in a place that is left-right symmetric to a place of the second myoelectric sensor that has output the second correlated myoelectric signal with respect to the limbs from among the plurality of first myoelectric signals;
calculating a similarity between the first and second correlated myoelectric signals; and
outputting the calculated similarity, wherein
in the selecting of the second correlated myoelectric signal, the at least one second myoelectric signal is selected based on the correlation between the sensor signal output by the detection sensor attached in a place where an acceleration changes according to the comparative motion and the second myoelectric signals output by the second myoelectric sensors for measuring a myoelectric potential that changes as a result of the comparative motion, and selecting the second correlated myoelectric signal includes:
- adding a root-mean-square value calculated from each of the plurality of second myoelectric signals to the predetermined strength or stronger of the myoelectric signal selected from among the plurality of second myoelectric signals,
- comparing a resultant value of the addition with a predetermined value, and
- selecting the myoelectric signal selected from among the plurality of second myoelectric signals as the second correlated myoelectric signal when the resultant value is equal to or larger than the predetermined value.

\* \* \* \* \*